United States Patent
Chen et al.

(10) Patent No.: US 12,144,846 B2
(45) Date of Patent: Nov. 19, 2024

(54) STRAIN FOR PRODUCING NATTOKINASE AND PRODUCTION METHOD THEREFOR

(71) Applicant: SUNGEN BIOSCIENCE CO., LTD., Guangdong (CN)

(72) Inventors: Jiepeng Chen, Shantou (CN); Lili Duan, Shantou (CN); Lin Hong, Shantou (CN); Yeyu Ji, Shantou (CN); Hongrui Chen, Shantou (CN); Chunli Cai, Shantou (CN); Liusong Hu, Shantou (CN); Zhikai Xu, Shantou (CN); Yufan Chen, Shantou (CN)

(73) Assignee: SUNGEN BIOSCIENCE CO., LTD., Shantou (CN)

( * ) Notice: Subject to any disclaimer, the term of this patent is extended or adjusted under 35 U.S.C. 154(b) by 627 days.

(21) Appl. No.: 17/424,761

(22) PCT Filed: Jul. 2, 2019

(86) PCT No.: PCT/CN2019/094334
§ 371 (c)(1),
(2) Date: Jul. 21, 2021

(87) PCT Pub. No.: WO2021/000247
PCT Pub. Date: Jan. 7, 2021

(65) Prior Publication Data
US 2022/0088154 A1 Mar. 24, 2022

(51) Int. Cl.
*A61K 38/48* (2006.01)
*C12N 1/20* (2006.01)
*C12N 9/54* (2006.01)
*C12P 21/02* (2006.01)
*C12R 1/125* (2006.01)

(52) U.S. Cl.
CPC ............ *A61K 38/482* (2013.01); *C12N 1/205* (2021.05); *C12N 9/54* (2013.01); *C12P 21/02* (2013.01); *A61K 2236/19* (2013.01); *C12N 2500/12* (2013.01); *C12N 2500/32* (2013.01); *C12N 2500/34* (2013.01); *C12N 2500/74* (2013.01); *C12N 2500/76* (2013.01); *C12N 2523/00* (2013.01); *C12R 2001/125* (2021.05)

(58) Field of Classification Search
CPC .. A61K 38/482; A61K 2236/19; C12N 1/205; C12N 9/54; C12N 2500/12; C12N 2500/32; C12N 2500/34; C12N 2500/74; C12N 2500/76; C12N 2523/00; C12P 21/02; C12R 2001/125
See application file for complete search history.

(56) References Cited

FOREIGN PATENT DOCUMENTS

| CN | 1857722 A | 11/2006 | | |
|---|---|---|---|---|
| CN | 101316608 A | 12/2008 | | |
| CN | 101560478 A | 10/2009 | | |
| CN | 101979531 A | 2/2011 | | |
| CN | 103695359 A | 4/2014 | | |
| CN | 107099487 A | 8/2017 | | |
| CN | 107129977 A | 9/2017 | | |
| CN | 107828685 A | 3/2018 | | |
| CN | 107841473 A | 3/2018 | | |
| CN | 109589405 A | 4/2019 | | |
| CN | 110408558 A | 11/2019 | | |
| EP | 1927365 A1 | * | 6/2008 | ........... A61K 35/742 |
| JP | 2019059705 A | 4/2019 | | |

OTHER PUBLICATIONS

Man, LL., Xiang, DJ. & Zhang, CL. Strain Screening from Traditional Fermented Soybean Foods and Induction of Nattokinase Production in Bacillus subtilis MX-6. Probiotics & Antimicro. Prot. 11, 283-294 (2019). https://doi.org/10.1007/s12602-017-9382-7 (Year: 2018).*
Chen C et al., Controlled conductivity at low pH in Protein L chromatography enables separation of bispecific and other antibody formats by their binding valency. MAbs. May/Jun. 2019;11(4):632-638. https://doi.org/10.1080/19420862.2019.1583996 (Year: 2019).*
Chinese Patent Application No. 201910588314.0, The First Office Action dated Sep. 29, 2022.
Japanese Patent Application No. 2021-540418, Notice of Reasons for Refusal dated Jul. 5, 2022.
Mar. 18, 2022—(EP) Extended European Search Report—App 19936116.3.
Mar. 26, 2020—International Search Report and Written Opininon of Appln No. PCT/CN2019/094334.
Man, L.L. et al. "Strain Screening from Traditional Fermented Soybean Foods and Induction of Nattokinase Production in Bacillus subtilis MX-6"; Probiotics and Antimicrobial Proteins, vol. 11, Feb. 6, 2018; pp. 283-294.
Liu, Z.M et al. "High-level extracellular production of recombinant nattokinase in Bacillus subtilis WB800 by multiple tandem promoters"; BMC Microbiology, vol. 19; May 7, 2019; chapter 89, pp. 1-14.

(Continued)

*Primary Examiner* — Louise W Humphrey
*Assistant Examiner* — Rachel Emily Martin
(74) *Attorney, Agent, or Firm* — Banner & Witcoff, Ltd.

(57) ABSTRACT

Disclosed are a strain for producing nattokinase and a production method therefor. In particular, the present invention involves a novel strain capable of producing nattokinase, i.e. *Bacillus subtilis* natto ST-1086, deposited at the China General Microbiological Culture Collection Center under CGMCC No. 17895. The present invention further involves a method for producing a nattokinase product by means of using the novel strain CGMCC No. 17895 of the present application, wherein the resulting nattokinase product can be used as a drug for dissolving thrombi. The present invention further involves the use of the nattokinase product of the present application for preparing a composition for dissolving thrombi and in a method for treating thrombi.

16 Claims, No Drawings

(56) References Cited

OTHER PUBLICATIONS

Xiong et al. "Study on liquid fermentation of nattokinase"; Chinese Journal of Bioprocess Engineering; vol. 10, No. 4; Jul. 2012; pp. 26-29.

* cited by examiner

STRAIN FOR PRODUCING NATTOKINASE AND PRODUCTION METHOD THEREFOR

CROSS-REFERENCE TO RELATED APPLICATIONS

This application is a U.S. National Stage application under 35 U.S.C. § 371 of International Application PCT/CN2019/094334 (published as WO 2021-000247 A1), filed Jul. 2, 2019. Each of these prior applications is hereby incorporated by reference in their entirety.

TECHNICAL FIELD

The present application relates to, but is not limited to, the field of microbial fermentation. Specifically, the present application relates to, but is not limited to, a strain for producing nattokinase and a method for producing nattokinase products.

BACKGROUND

Nattokinase is internationally recognized as one of the most important active molecules for the prevention, management and treatment of human cardiovascular and cerebrovascular diseases, and it is a trace active substance produced by fermentation of *Bacillus subtilis* natto. Over the years, it has been widely used in food, dietary supplements and domestic health care products market. The raw materials of nattokinase dietary supplements are in great demand in the international and domestic markets.

At present, around the world, nattokinase is mainly produced in Japan, Taiwan and the United States. Nattokinase produced in Japan is extracted from natto fermented by *Bacillus subtilis* natto, with the activity of 10000-22000 FU/g, which is equivalent to 67000-147400 IU/g. In Japan, there are mainly four producers of nattokinase: Nabio, Japan Bio Science Laboratory Co., Ltd., Daiwa and a subsidiary corporation of Honda. The first and largest producer of nattokinase is Japan Bio Science Laboratory Co., Ltd., which occupies most of the markets in Taiwan and Japan. Nattokinase powder produced by Daiwa also occupies a certain market share in Japan. The nattokinase raw materials of these two companies are for their own use, and are not for external sales. Japan Bio Science Laboratory Co., Ltd. and Daiwa employ old technologies, and their products have a single efficacy, lack the protection from viscous substances, are easily deactivated and have poor stability, but the costs are low. The subsidiary corporation of Honda is substantially the same as Japan Bio Science Laboratory Co., Ltd., and has patents for nattokinase. Nabio of Japan is a rising star in the production of nattokinase, of which the activity of nattokinase products reaches 22000 FU/g, equivalent to 147400 IU/g, but with a high price. The technology of producing nattokinase in Taiwan comes from Japan. Nattokinase produced in the United States is extracted from *Aspergillus* fermentation products, which does not contain viscous substances such as the bacteria and vitamin K2, and can be called "thrombolytic enzyme".

It was reported that nattokinase yield of 3232 IU/ml (equivalent to 482.4 FU/ml) was achieved by liquid fermentation of *Bacillus subtilis* natto (see XIONG Qiang, et al., *Study on Liquid Fermentation Conditions of Nattokinase*, Chinese Journal of Bioprocess Engineering, 2012, Vol. 10, No. 4, pp. 26-29).

In China, the natto industry is in the stage of rapid development. Fresh natto and a series of natto foods with natto extract powder as main raw materials such as compound drinks, candies, biscuits and health foods have become a major consumption hotspot. However, due to the instability of nattokinase and the susceptibility to denaturation in purification process, it is very difficult to obtain pure nattokinase at present. And, there is no pure nattokinase or its preparations for sale in China and foreign countries, nor nattokinase drugs at present. Therefore, the present application aims to provide a method for producing and purifying nattokinase.

SUMMARY

The following is a summary of the subject matters described in detail herein. This summary is not intended to limit the protection scope of the claims.

In order to overcome the shortcomings of the prior art and meet the market demands, an object of the present application is to provide a novel strain capable of producing nattokinase.

After many years of intensive and careful research, the applicant isolated *Bacillus subtilis* natto strains from fresh commercial natto, and used them as the starting strains to be mutagenized and a novel *Bacillus subtilis* natto ST1086 was obtained. The mutant strain was deposited at China General Microbiological Culture Collection Center under CGMCC No. 17895, with the address of NO. 3 of Court NO. 1 Beichen West Road, Chaoyang District, Beijing, Institute of Microbiology, Chinese Academy of Sciences, on Jun. 5, 2019. The applicant isolated strains from the fresh commercial natto, and obtained a strain of *Bacillus subtilis* natto ST102 producing nattokinase. The strain ST102 was used as the starting strain for UV mutagenesis. After 50 generations of UV mutagenesis, a morphological mutant strain ST1086 was obtained, and the yield of nattokinase was increased by 11 fold. The morphological mutation and the yield of nattokinase were stable after several generations of subculture.

The novel strain CGMCC No. 17895 provided by the present application has the following microbiological characteristics: Gram-positive bacterium, central spore, spore size of 0.6-0.8 μm×1.0-1.5 μm, bacterium width of 1 μm and bacterium length of 2-3 μm. On an LB agar medium, its colony has a plump, wrinkled and white surface, and is convex and ropy. The diameter of the colony is 0.3-0.5 cm, and there is no pigment. Spores appear after 10 hours of culture.

In an aspect of the present application, it is provided a method for producing a nattokinase product by using the novel strain CGMCC No. 17895 of the present application, including culturing the strain CGMCC No. 17895 of the present application in a medium to produce nattokinase in the medium. The culturing may be carried out in a device conventional or known in the art and under conditions conventional or known in the art, for example, using a shaking flask at a rotational speed conventional or known in the art; or carried out in a conventional fermenter, such as a 5 L fermenter or a 5T fermenter.

In some embodiments, the medium includes a carbon source substance and a nitrogen source substance, and the ratio of the carbon source substance to the nitrogen source substance is 10:1 to 1:2. In some embodiments, the carbon source substance is selected from one or more of glucose, sucrose, maltose, fructose and glycerol, and the nitrogen source substance is selected from one or more of yeast powder, peptone, soybean powder and chickpea powder.

In some other embodiments, the medium further includes an organic substance, an inorganic substance, or a mixture of an organic substance and an inorganic substance, which promotes the growth of microorganisms and improves the yield of nattokinase. In some embodiments, the organic substance is one or more of serine, glycine and alanine, and the inorganic substance is a magnesium salt or a sodium salt. Preferably, the inorganic substance is magnesium sulfate, magnesium chloride, sodium chloride.

In some other embodiments, the culturing is carried out at 35-45° C., preferably 37-40° C. In some embodiments, the culturing lasts 10-48 hours, preferably 12-24 hours.

According to some embodiments, the method includes adding a carbon source substance or a nitrogen source substance, or a mixture of a carbon source substance and a nitrogen source substance during fermentation. In some embodiments, the method further includes the following steps: (1) solid-liquid separation to separate the bacteria and the supernatant; (2) separation with an ultrafiltration membrane to obtain a concentrated solution of nattokinase, the molecular weight of the ultrafiltration membrane preferably ranging from 1,000 to 50,000 D, more preferably from 10,000 to 30,000 D; (3) washing with 1 mmol/L NaCl solution to obtain a conductivity of the concentrated solution of nattokinase ≤300 μs/cm, preferably ≤200 μs/cm, more preferably ≤100 μs/cm; and (4) drying, preferably spray drying, freeze drying, vacuum drying. In some embodiments, a solid-liquid separation method conventional or known in the art, such as ceramic membrane separation or centrifugation, is used for the solid-liquid separation. In some embodiments, a protective agent is added in the drying step, and the protective agent is preferably soybean protein powder, collagen powder, dietary fibers, microcrystalline cellulose, corn starch or a combination thereof, more preferably 5%-25% of soybean protein powder and 2.5%-12.5% of dietary fibers.

According to some embodiments, the activity of the nattokinase product obtained by the method of the present application is 65,000-750,000 FU/g, which is equivalent to 436,000 IU/g-5,025,000 IU/g.

In another aspect, the present application further provides a method for preparing a nattokinase product from a culture solution resulting from the fermentation of the novel strain CGMCC No. 17895 of the present application. In some embodiments, the method includes the following steps:

(1) solid-liquid separation, carried out by a solid-liquid separation method conventional or known in the art, such as ceramic membrane separation, centrifugation, to separate bacteria and fermentation supernatant;

(2) separation with an ultrafiltration membrane to obtain a concentrated solution of nattokinase, the molecular weight of the ultrafiltration membrane preferably ranges from 1,000 to 50,000 D, more preferably from 10,000 to 30,000 D;

(3) washing with an isotonic salt solution to obtain a conductivity of the concentrated solution of nattokinase ≤300 μs/cm, preferably ≤200 μs/cm, and more preferably ≤100 μs/cm; and (4) drying, preferably spray drying, freeze drying, vacuum drying.

In some embodiments, a protective agent conventional or known in the art, such as soybean protein powder, collagen powder, dietary fibers, microcrystalline cellulose, corn starch or a combination thereof, preferably 5%-25% of soybean protein powder and 2.5%-12.5% of dietary fibers, is added during drying.

By adopting the strain CGMCC No. 17895 of the present application and the fermentation method of the present application, the period is reduced to 16-24 hours, the yield is as high as 12,000 IU/ml (equivalent to 1791.0 FU/ml), the activity of the final nattokinase product is 65,000-750,000 FU/g, and the preparation process is more robust.

Other aspects will become apparent after reading and understanding the embodiments.

DETAILED DESCRIPTION

The present application will be further described below by examples, and the description is not intended to further limit the content of the present application. Those of ordinary skills in the art will appreciate that modifications or equivalent substitutions may be made to the technical solutions of the present application without departing from the spirit and scope of the technical solutions of the present application, all of which should be contained within the scope of the claims of the present application.

In the present application, the activity of nattokinase is determined by the following methods.

Nattokinase Activity Assay (I)

Test Solution

1. PBS (Phosphate Buffer Saline) Buffer Solution:

0.01 mol/L phosphate buffer solution (pH7.5): 3.58 g of disodium hydrogen phosphate ($Na_2HPO_4 \cdot 12H_2O$) was weighed out, and dissolved by adding double distilled water and diluted to 1000 mL to obtain solution I; 0.78 g of sodium dihydrogen phosphate ($NaH_2PO_4 \cdot 2H_2O$) was taken and dissolved by adding double distilled water and diluted to 500 mL to obtain solution II; about 84 mL of solution I and about 16 mL of solution II were taken and mixed until the pH value was 7.5.

0.01 mol/L phosphate buffer solution (pH7.5) was mixed with 0.9% sodium chloride solution (1:17) to obtain a PBS buffer solution.

2. 1.5% agarose solution: 1.5 g agarose was taken, added with 100 mL PBS buffer solution, dissolved by heating, and subjected to a 50° C. water bath to keep the temperature constant.

3. Fibrinogen solution: an appropriate amount of fibrinogen was taken and added with PBS buffer solution to prepare a solution containing 1.5 mg coagulable protein per 1 mL.

4. Thrombin solution: thrombin was taken and added with 0.9% sodium chloride solution to prepare a solution containing 1BP unit per 1 mL.

5. Preparation of a Urokinase Standard Solution:

5.1 Urokinase standard solution (1000 IU/mL): A bottle of urokinase was taken, and dissolved by adding PBS buffer solution according to the labeled titer to obtain 1000 IU/mL urokinase standard solution.

5.2 Preparation of urokinase working standard solution, which was as follows:

TABLE 1

| concentration of urokinase working standard solution (IU/mL) | sampling volume of urokinase standard solution (μL) | sampling volume of PBS buffer solution (μL) |
|---|---|---|
| 1000 | 100 | 0 |
| 800 | 80 | 20 |
| 600 | 60 | 40 |
| 500 | 50 | 50 |
| 400 | 40 | 60 |
| 200 | 20 | 80 |
| 100 | 10 | 90 |
| 50 | 10 | 190 |
| 25 | 10 | 390 |

Plate Preparation 39 mL of fibrinogen solution warmed in a 50° C. water bath for 5 min was placed in a beaker, and added with 39 mL of 50° C. agarose solution and 3.0 mL of thrombin solution while stirring. The solution was mixed well immediately, all of which was quickly poured into a 14 cm Petri dish, and placed horizontally at room temperature for 1 hour. Several holes were punched in the fibrin plate with a small stainless steel tube (puncher) having a diameter of 3 mm.

Assay

10 μL of each of the urokinase standard solutions with different concentrations were accurately measured, spotted onto a single agarose fibrin plate, covered, and put in a 37° C. incubator to react for 18 hours. The plate was taken out for measuring the diameter of the solusphere. The solusphere area was calculated, and the logarithm of solusphere area was taken as abscissa and the logarithm of concentration was taken as ordinate to make a regression curve and obtain the corresponding regression equation.

According to the pre-estimated activity of nattokinase, a nattokinase sample was accurately weighed out and placed in a volumetric flask, and dissolved with a suitable amount of PBS buffer solution. The solution was subjected to ultrasonic treatment for 15 minutes, and the volume thereof was made to the marking, so that the final spotting concentration was 200-400 IU/mL. 10 μL of the nattokinase sample solution was accurately measured, and spotted onto an agarose fibrin plate, covered, and put in a 37° C. incubator for reaction for 18 hours. The plate was taken out for measuring the diameter of the solusphere to calculate the solusphere area. The solusphere area of the sample was applied to the regression equation to calculate the nattokinase activity of the sample solution.

Calculation of Nattokinase Activity:

$$X = C \times V/M$$

wherein: X: nattokinase activity of the sample, IU/g;
C: nattokinase activity of the sample solution calculated by the regression equation, IU/mL;
V: total diluted volume of the sample, mL;
M: mass of the sample, g.

Nattokinase Activity Assay (II)

The nattokinase activity in FU is defined as:

$$FU/mL \text{ or } FU/g = \frac{0.01 \text{ unit of } OD_{275} \text{ nm increase by fibrin decomposition}}{\text{reaction time (min)} * \text{volume of sample solution (mL)}}$$

Nattokinase activity is analyzed according to the nattokinase activity analysis method (No. 104022640) of Japan Food Research Laboratories.

Enzyme Reaction Group (1) 1.4 mL PBS buffer solution and 0.4 mL 0.72% fibrinogen solution were added into a test tube, mixed well, and placed in a 37±0.3° C. water bath for reaction for 5 min.

(2) 0.1 mL 20 U/mL thrombin solution was further added into the above test tube. The solution was mixed well and placed in a 37±0.3° C. water bath for reaction for 10 min.

(3) When the solution in step (2) has reacted accurately for 10 minutes, 0.1 mL of the test sample solution was accurately added, and the solution was mixed well, and placed in a 37±0.3° C. water bath for enzyme reaction for 60 minutes. The solution was shaken well at 30 min and 50 min of the reaction, respectively.

(4) When the solution in step (2) has reacted accurately for 60 min, 2 mL 0.2M trichloroacetic acid solution was added to terminate the enzyme reaction, and the solution was placed in a 37±0.3° C. water bath for reaction for 20 min.

Negative Control Tube (1) The reaction is the same as the steps (1) and (2) of the enzyme reaction group, and when the reaction had proceeded accurately for 10 minutes, 2 mL 0.2 M trichloroacetic acid solution was added first.

(2) then 0.1 mL of test sample solution was added, and the solution was mixed well, and placed in a 37±0.3° C. water bath for reaction for 20 min.

(3) After the reaction was terminated, the test tube was centrifuged at 12000 rpm for 10 min.

(4) The supernatant was transferred to a clean test tube as a negative control tube. Using the negative control tube as blank, optical density (OD) of the enzyme reaction group was measured at 275 nm, and recorded.

Nattokinase activity was calculated as follows:

$$X = \frac{Ar - Ac}{0.01 \times 60 \times 0.1} \times \text{dilution of the sample}$$

Wherein: X: nattokinase activity of the sample, FU/g or FU/mL;
Ar: OD value of the enzyme reaction group;
Ac: OD value of the negative control group;
Ar-Ac: the numerical value must be between 0.050 and 0.080;
60: representing reaction time (min);
0.1: representing sample volume (mL).

Example 1: Isolation of Nattokinase-Producing *Bacillus subtilis* Natto from Commercial Natto Natto (purchased from Japan Bio Science Laboratory Co., Ltd.) was dissolved and diluted with sterile water, then smeared on a solid LB medium plate, and cultured at a constant temperature of 37° C. for 24 hours. White colonies grew on the surface of the plate, which exhibited ropy phenomenon when picked with an inoculation needle. The white colonies were transferred to a LB slant medium, cultured at 37° C. for 24 hours, inoculated into a fermentation medium (20 ml in a 100 ml Erlenmeyer flask, medium formula: glucose 2%, sucrose 2%, soybean powder 3%, magnesium sulfate 0.01%, sodium chloride 0.5%, and serine 0.08%) with an inoculating loop, shaken at 37° C. at 270 rpm for 20 hours, and centrifuged to take the supernatant. The content of nattokinase was determined by the agarose fibrin plate method, and strains with relatively large solusphere diameters were selected to finally identify *Bacillus subtilis* natto for producing nattokinase.

Example 2: Mutagenesis of Strains for Producing Nattokinase

*Bacillus subtilis* natto obtained in Example 1 was used as the starting strain for UV mutagenesis (ultraviolet wavelength: 200-300 nm, irradiation distance: 15-30 cm, and irradiation time: 20 s), and after 50 generations of mutagenesis, a mutant strain ST-1086 was obtained. The mutant strain ST-1086 has the following microbiological characteristics: Gram-positive bacterium, central spore, spore size of 0.6-0.8 μm×1.0-1.5 μm, bacterium width of 1 μm and bacterium length of 2-3 μm. On an LB agar medium, the colony has a plump, wrinkled and white surface, is convex and ropy, has a diameter of 0.3-0.5 cm, and has no pigments, and spores appear after 10 hours of culture. The mutant strain ST-1086 was deposited at China General Microbiological Culture Collection Center, with the address of NO. 3 of Court NO. 1 Beichen West Road, Chaoyang District, Beijing, Institute of Microbiology, Chinese Academy of Sciences, on Jun. 5, 2019, under the access number of CGMCC No. 17895.

Example 3: Seed Preparation

The starting strain and the CGMCC No. 17895 strain obtained in Example 2 were respectively inoculated into 20 ml of seed medium (see Table 1) and incubated at 37-40° C., 150-300 rpm shaking in a incubator for 3-16 hours, obtaining a seed culture solution.

TABLE 2

| Seed medium: | |
|---|---|
| components | content % |
| glucose | 1.0 |
| tryptone | 1.0 |
| yeast extract | 0.5 |
| NaCl | 1.0 |
| pure water | making up to a volume of 100 ml |
| pH | 7.0 |

Example 4: Fermentation in a 5 L Fermenter

The seed culture solution obtained in Example 3 was inoculated into a basal medium (see Table 2) at an inoculation amount of 20% of the fermentation medium, and cultured at 40° C. After 30 minutes of culture, a feed medium (see Table 3) was added in a fed-batch manner, and 200 ml of feed medium was added every half hour for 10.5 hours, with a total of 2 L feed medium being added. The pH value in the culture process kept unadjusted, and the concentration of oxygen dissolved was controlled to be above 30%. The fermentation period was 17 hours. Nattokinase content was determined by the fibrin plate method.

TABLE 3

| Basal medium | |
|---|---|
| components | content % |
| soybean powder | 0.5 |
| sucrose | 0.9 |
| glucose | 0.1 |
| magnesium sulfate | 0.05 |
| sodium chloride | 0.5 |
| serine | 0.01 |
| sodium hydroxide | 0.003 |
| pure water | making up to a volume of 100 ml |

TABLE 4

| Feed medium | |
|---|---|
| components | content % |
| soybean powder | 10 |
| glucose | 8 |
| sucrose | 8 |
| sodium hydroxide | 0.04 |
| pure water | making up to a volume of 100 ml |

The yield of nattokinase by the starting strain using this method was 800 IU/ml (equivalent to 119.4 FU/ml). The fermentation broth obtained was subjected to solid-liquid separation with a ceramic membrane, and the resultant dialysate was concentrated with an ultrafiltration membrane having a molecular weight of 10,000 D. The nattokinase activity of the concentrated solution was 7,000 IU/ml (equivalent to 1044.8 FU/ml). To the concentrated solution of nattokinase, 15% soybean protein powder and 5% dietary fibers (wheat-derived water-soluble dietary fibers purchased from Roquette, France) was added and dissolved. Then the concentrated solution of nattokinase was spray-dried. Natto powder with activity of 1,500 FU/g (equivalent to 10,050 IU/g) was obtained.

The yield of nattokinase of CGMCC No. 17895 strain of the present application was 7,500 IU/ml (equivalent to 1119.4 FU/ml). The fermentation broth obtained was subjected to solid-liquid separation with a ceramic membrane, and the resultant dialysate was concentrated with an ultrafiltration membrane having a molecular weight of 10,000 D. The nattokinase activity of the concentrated solution was 150,000 IU/ml (equivalent to 22388.1 FU/ml). The concentrated solution of nattokinase obtained was added with 12% soybean protein powder and 6% dietary fibers and was spray dried. Natto powder with activity of 58,000 FU/g (equivalent to 390,000 IU/g) was obtained.

Example 5

This example is different from Example 4 in that the feed medium contained 0.16% serine. The nattokinase fermentation yield of CGMCC No. 17895 strain of the present application was 12,000 IU/ml (equivalent to 1791.0 FU/ml).

Example 6

This example is different from Example 4 in that the feed medium contained 0.16% glycine. The nattokinase fermentation yield of CGMCC No. 17895 strain of the present application was 9,000 IU/ml (equivalent to 1343.3 FU/ml).

Example 7

This example is different from Example 4 in that the feed medium contained 0.16% alanine. The nattokinase fermentation yield of CGMCC No. 17895 strain of the present application was 10,000 IU/ml (equivalent to 1492.5 FU/ml).

Example 8

This example is different from Example 4 in that the feed medium contained 0.16% serine and 0.16% glycine. The nattokinase fermentation yield of CGMCC No. 17895 strain of the present application was 10,500 IU/ml (equivalent to 1567.2 FU/ml).

Example 9

This example is different from Example 4 in that the feed medium contained 0.16% serine and 0.16% alanine. The nattokinase fermentation yield of CGMCC No. 17895 strain of the present application was 11,000 IU/ml (equivalent to 1641.8 FU/ml).

Example 10

This example is different from Example 4 in that the feed medium contained 0.16% glycine and 0.16% alanine. The nattokinase fermentation yield of CGMCC No. 17895 strain of the present application was 9,500 IU/ml (equivalent to 1417.9 FU/ml).

Example 11

This example is different from Example 4 in that the feed medium contained 0.16% serine, 0.16% glycine and 0.16% alanine. The nattokinase fermentation yield of CGMCC No. 17895 strain of the present application was 10,300 IU/ml (equivalent to 1537.3 FU/ml).

Example 12

The fermentation broth of CGMCC No. 17895 in Example 4 was subjected to solid-liquid separation by a ceramic membrane with pore size of 0.1 μm, to remove solid particles such as bacteria and media to obtain a nattokinase-containing liquid. The nattokinase-containing liquid obtained was filtered and concentrated by an ultrafiltration membrane with a molecular weight cut-off of 10,000 D to obtain a concentrated solution of nattokinase. The concentrated solution of nattokinase obtained was treated with ammonium sulfate at 30% saturation to remove impurities, and further treated with ammonium sulfate at 70% saturation to remove some pigments and polysaccharides and obtain nattokinase precipitate. The nattokinase precipitate was desalted with sephadex G25 filler by eluting with a phosphate buffer solution, with a loading volume of 20% CV (column volume) and at a flow rate of 40 cm/h, to collect the desalted nattokinase solution. The desalted nattokinase solution was purified by SP sepharose FF filler (purchased from GE), with a loading volume of 80-120 mg/ml and at a flow rate of 120 cm/h, to obtain a nattokinase solution from which pigments, polysaccharides and some impurity proteins were removed. The concentrated solution with pigments, polysaccharides and some impurity proteins being removed was subjected to column chromatography with a molecular sieve filler superdex 75, to remove the remaining impurity protein bands, with a loading volume of 5% CV and at a flow rate of 20 cm/h to collect a collection solution containing single band of nattokinase. The collection solution of single band of nattokinase was freeze-dried by a lyophilizer to obtain a pure nattokinase powder of 7,000,000 FU/g (equivalent to 46,900,000 IU/g).

TABLE 5

| | activity concentration IU/ml (g) | recovery ratio % |
|---|---|---|
| fermentation broth | 7500 | 100% |
| concentrated solution | $1.5 \times 10^5$ | 95% |
| salting out with 30% ammonium sulfate | $1.4 \times 10^5$ | 93% |
| salting out with 70% ammonium sulfate | $2.0 \times 10^5$ | 90% |
| Sephadex G25 column chromatography | $1.4 \times 10^5$ | 81% |
| SP sepharose FF | $3.1 \times 10^5$ | 50% |
| Superdex 75 | $5.2 \times 10^5$ | 42% |
| lyophilized powder | $4.7 \times 10^7$ | 38% |

Example 13

The object of this example is to purify nattokinase of CGMCC No. 17895 strain according to a purification method in the literature, and investigate the change of nattokinase activity during the purification process.

The fermentation broth of CGMCC No. 17895 in Example 4 was subjected to solid-liquid separation by a ceramic membrane with pore size of 0.1 μm to remove solid particles such as bacteria and media to obtain a nattokinase-containing liquid. The nattokinase-containing liquid obtained was filtered and concentrated by an ultrafiltration membrane with a molecular weight cut-off of 10,000 D to obtain a 7,000 IU/ml concentrated solution of nattokinase. The concentrate solution was subjected to precipitation with 30% ammonium sulfate and then precipitation with 60% ammonium sulfate to remove some pigments and polysaccharides, thus obtaining nattokinase precipitate. The precipitate was dissolved by 2M ammonium sulfate solution to form a 5% solution, subjected to Phenyl Sepharose hydrophobic column chromatography, with a loading volume of 20-60 mg/ml and at a flow rate of 60 cm/h, then eluted with a linear gradient of 2M-OM ammonium sulfate solution, with 20 column volumes and at a flow rate of 100 cm/h. The eluate was collected in fractions. The purity of nattokinase in the eluate was detected by SDS-PAGE. A pure nattokinase product with 95% purity was obtained, and the chromatography effluent was directly freeze-dried to obtain 5,000,000 FU/g (33,500,000 IU/g) pure nattokinase powder.

TABLE 6

| | activity concentration IU/ml (g) | recovery ratio % |
|---|---|---|
| fermentation broth | 800 | 100% |
| concentrated solution | 7000 | 95% |
| salting out with 30% ammonium sulfate | 6900 | 93% |
| salting out with 60% ammonium sulfate | 15000 | 89% |
| Phenyl Sepharose hydrophobic column chromatography | 5000 | 44% |
| lyophilized powder | $3.35 \times 10^7$ | 40% |

Example 14

This example is different from Example 12 in that the fermentation broth of the starting strain in Example 4 was used and 6,000,000 FU/g (equivalent to 40,200,000 IU/g) pure nattokinase powder was obtained.

TABLE 7

| | activity concentration IU/ml | (g)recovery ratio % |
|---|---|---|
| fermentation broth | $8.0 \times 10^2$ | 100% |
| concentrated solution | $1.1 \times 10^4$ | 95% |
| salting out with 30% ammonium sulfate | $1.4 \times 10^4$ | 93% |
| salting out with 70% ammonium sulfate | $2.0 \times 10^4$ | 90% |
| Sephadex G25 column chromatography | $1.4 \times 10^4$ | 83% |
| SP sepharose FF | $2.9 \times 10^4$ | 49% |
| Superdex 75 | $4.6 \times 10^4$ | 35% |
| lyophilized powder | $4.0 \times 10^7$ | 32% |

It can be seen from the results of Example 12 and Example 13 that compared with the prior art methods, the purification method of the present application can significantly increase the activity concentration of pure nattokinase product.

It can be seen from the results of Example 12 and Example 14 that compared with the starting strain, CGMCC No. 17895 strain of the present application can realize a pure product with a higher nattokinase activity concentration.

Example 15

This example is different from Example 5 in that the fermentation broth obtained by fermenting CGMCC No. 17895 strain of the present application was concentrated with a 10,000 D ultrafiltration membrane and then washed with 0.1 mmol/L NaCl solution until the conductivity reached 300 μs/cm. The conductivity was measured with a conductivity meter. The activity of the resultant concentrated solution of nattokinase was 300,000 IU/ml (equivalent to 45,000 FU/ml). 5% microcrystalline cellulose and 5% dietary fibers were added to the concentrated solution and spray drying is conducted. Spray drying conditions: inlet air temperature: 200° C., outlet air temperature: 45° C., fan speed: 70 R/min, feed rate: 45 L/h, and drying yield: 45%. The activity of the resultant natto powder was 101,000 FU/g (678,000 IU/g).

Example 16

This example is different from Example 5 in that the fermentation broth obtained by fermenting CGMCC No. 17895 strain of the present application was concentrated with a 10,000 D ultrafiltration membrane and then washed with 0.1 mmol/L NaCl solution until the conductivity reached 300p/cm. The conductivity was measured with a conductivity meter. The activity of the resultant concentrated solution of nattokinase was 300,000 IU/ml (equivalent to 45,000 FU/ml). 5% soybean protein powder and 5% dietary fibers were added to the concentrated solution and spray drying is conducted, and the drying yield was 80%. The activity of the resultant natto powder was 180,000 FU/g (equivalent to 1,206,000 IU/g). Using soybean protein powder as a protein protective agent can improve the stability of nattokinase; and microcrystalline cellulose was only an excipient, which improves the solid content of the concentrated solution and is beneficial to the spray drying process.

Example 17

This example is different from Example 5 in that the fermentation broth obtained by fermenting CGMCC No. 17895 strain of the present application was concentrated with a 10,000 D ultrafiltration membrane and then washed with 0.1 mmol/L NaCl solution until the conductivity reached 200 μs/cm. The activity of the resultant concentrated solution of nattokinase was 300,000 IU/ml (equivalent to 45,000 FU/ml). 15% soybean protein powder and 7.5% dietary fibers were added to the concentrated solution and spray drying is conducted, and the drying yield was 90%. The activity of the resultant natto powder was 129,000 FU/g (861,000 IU/g).

Example 18

This example is different from Example 5 in that the fermentation broth obtained by fermenting CGMCC No. 17895 strain of the present application was concentrated with a 10,000 D ultrafiltration membrane and then washed with 0.1 mmol/L NaCl solution until the conductivity reached 100p/cm. The activity of the resultant concentrated solution of nattokinase was 300,000 IU/ml (equivalent to 45,000 FU/ml). 15% soybean protein powder, 7.5% dietary fibers and 5% microcrystalline cellulose were added to the concentrated solution and spray drying is conducted, and the drying yield was 98%. The activity of the resultant natto powder was 124,000 FU/g (equivalent to 832,000 IU/g).

Example 19

This example is different from Example 5 in that the fermentation broth obtained by fermenting CGMCC No. 17895 strain of the present application was concentrated with a 10000 D ultrafiltration membrane and then washed with purified water until the conductivity reached 300 μs/cm. The activity of the resultant concentrated solution of nattokinase was 250,000 IU/ml (37,000 FU/ml). 5% soybean protein powder and 5% dietary fiber were added to the concentrated solution and spray drying is conducted, and the drying yield was 80%. The activity of the resultant natto powder was 164,000 FU/g (1,100,000 IU/g).

Example 20

This example is different from Example 5 in that the fermentation broth obtained by fermenting CGMCC No. 17895 strain of the present application was concentrated with a 10000 D ultrafiltration membrane and then washed with purified water until the conductivity reached 200 μs/cm. The activity of the resultant concentrated solution of nattokinase was 240,000 IU/ml (36,000 FU/ml). 15% soybean protein powder and 7.5% dietary fiber were added to the concentrated solution and spray drying is conducted, and the drying yield was 90%. The activity of the resultant natto powder was 108,000 FU/g (724,000 IU/g).

Example 21

This example is different from Example 5 in that the fermentation broth obtained by fermenting CGMCC No. 17895 strain of the present application was concentrated with a 10000 D ultrafiltration membrane and then washed with purified water until the conductivity reached 100 μs/cm. The activity of the resultant concentrated solution of nattokinase was 230,000 IU/ml (34,000 FU/ml). 15% soybean protein powder, 7.5% dietary fibers and 5% microcrystalline cellulose were added to the concentrated solution and spray drying is conducted, and the drying yield was 98%. The activity of the resultant natto powder was 97,000 FU/g (647,000 IU/g).

Example 22

This example is different from Example 5 in that the fermentation broth obtained by fermenting CGMCC No. 17895 strain of the present application was concentrated with a 10000 D ultrafiltration membrane and then washed with purified water until the conductivity reached 100 μs/cm. The activity of the resultant concentrated solution of nattokinase was 230,000 IU/ml (34,000 FU/ml). The concentrated solution was spray dried with a drying yield of 50%. The activity of the resultant natto powder was 210,000 FU/g (1,420,000 IU/g).

Example 23

The natto powders obtained in Example 22, Example 15, Example 16, Example 17 and Example 18 were respectively compressed to tablets to examine the stability of different auxiliary materials for the preparation process. Compressing process: 30% of fish collagen, 10% of maltodextrin, 10% of lactose and 30% of microcrystalline cellulose were added to natto powder, the raw materials and auxiliary materials were passed through a 80 mesh sieve separately, mixed, granulated and compressed to tablets and the activities of nattokinase before and after compressing were determined. The results were as follows:

TABLE 8

|  | Example 22 natto powder | Example 15 natto powder | Example 16 natto powder | Example 17 natto powder | Example 18 natto powder |
| --- | --- | --- | --- | --- | --- |
| Nattokinase activity after mixing | 78,600 FU/g (527,000 IU/g) | 37,800 FU/g (253,000 IU/g) | 67,500 FU/g (452,000 IU/g) | 48,000 FU/g (322,000 IU/g) | 46,000 FU/g (308,000 IU/g) |
| Nattokinase activity after granulation | 57,300 FU/g (384,000 IU/g) | 31,000 FU/g (208,000 IU/g) | 53,000 FU/g (355,000 IU/g) | 44,000 FU/g (295,000 IU/g) | 45,000 FU/g (301,000 IU/g) |
| Nattokinase activity after compressing | 35,400 FU/g (237,000 IU/g) | 22,700 FU/g (152,000 IU/g) | 46,000 FU/g (308,000 IU/g) | 41,000 FU/g (275,000 IU/g) | 44,600 FU/g (299,000 IU/g) |
| total yield | 45% | 60% | 68% | 85% | 97% |

What we claim is:

1. A *Bacillus subtilis* natto strain, deposited at China General Microbiological Culture Collection Center under CGMCC No. 17895.

2. A method for producing a nattokinase product, comprising culturing the *Bacillus subtilis* natto strain according to claim 1 in a medium to produce nattokinase in the medium.

3. The method according to claim 2, wherein the medium comprises a carbon source substance and a nitrogen source substance, and the ratio of the carbon source substance to the nitrogen source substance is 10:1 to 1:2.

4. The method according to claim 3, wherein the carbon source substance is selected from one or more of glucose, sucrose, maltose, fructose and glycerol.

5. The method according to claim 3, wherein the nitrogen source substance is selected from one or more of yeast powder, peptone, soybean powder and chickpea powder.

6. The method according to claim 2, wherein the medium further comprises an organic substance, an inorganic substance, or a mixture of an organic substance and an inorganic substance, which promotes the growth of microorganisms and improves the yield of nattokinase.

7. The method according to claim 6, wherein the organic substance is one or more of serine, glycine and alanine.

8. The method according to claim 6, wherein the inorganic substance is a magnesium salt or a sodium salt.

9. The method according to claim 2, wherein the culturing is carried out at 35-45° C.

10. The method according to claim 2, wherein the culturing lasts 10-48 hours.

11. The method according to claim 2, comprising adding a carbon source substance or a nitrogen source substance, or a mixture of a carbon source substance and a nitrogen source substance during fermentation.

12. The method according to claim 2, further comprising the steps of:
(1) solid-liquid separation to separate the bacteria and the supernatant;
(2) separation with an ultrafiltration membrane to obtain a concentrated solution of nattokinase, wherein the molecular weight cutoff of the ultrafiltration membrane ranges from 1,000 to 50,000D;
(3) washing with 1 mmol/L isotonic NaCl solution at a conductivity of ≤300 μs/cm to obtain a concentrated solution of nattokinase; and
(4) drying the concentrated nattokinase solution of step (3).

13. The method according to claim 12, wherein the solid-liquid separation is carried out using a ceramic membrane or by centrifugation.

14. The method according to claim 12, wherein a protective agent is added in the drying step, and the protective agent is soybean protein powder, collagen powder, dietary fibers, microcrystalline cellulose, corn starch or a combination thereof.

15. The method according to claim 4, wherein the nitrogen source substance is selected from one or more of yeast powder, peptone, soybean powder and chickpea powder.

16. The method according to claim 7, wherein the inorganic substance is a magnesium salt or a sodium salt.

* * * * *